United States Patent
Huang et al.

(10) Patent No.: US 6,863,652 B2
(45) Date of Patent: Mar. 8, 2005

(54) POWER CONSERVING ADAPTIVE CONTROL SYSTEM FOR GENERATING SIGNAL IN PORTABLE MEDICAL DEVICES

(75) Inventors: Johnnie W. Huang, Hillsborough, CA (US); Matthew Mozur, Danvers, MA (US); Clifford Mark Kelly, Windham, NH (US); Michael Joseph Riley, Groveland, MA (US); Michael J. Bernstein, San Ramon, CA (US)

(73) Assignee: Draeger Medical Systems, Inc., Danvers, MA (US)

( * ) Notice: Subject to any disclaimer, the term of this patent is extended or adjusted under 35 U.S.C. 154(b) by 0 days.

(21) Appl. No.: 10/385,373

(22) Filed: Mar. 10, 2003

(65) Prior Publication Data

US 2004/0002637 A1 Jan. 1, 2004

Related U.S. Application Data

(60) Provisional application No. 60/363,791, filed on Mar. 13, 2002.

(51) Int. Cl.[7] .................................................. A61B 5/00
(52) U.S. Cl. ...................... 600/300; 600/301; 600/306; 600/322; 315/291; 315/224; 315/307
(58) Field of Search ............................... 600/300, 301, 600/306, 309, 310, 322, 323, 334, 336; 315/291, 307, 308, 224, 248, 149, 151, 158

(56) References Cited

U.S. PATENT DOCUMENTS

| | | | |
|---|---|---|---|
| 4,281,645 A | 8/1981 | Jobsis | 128/633 |
| 4,653,498 A | 3/1987 | New, Jr. et al. | 128/633 |
| 4,859,057 A | 8/1989 | Taylor et al. | 356/41 |
| 4,892,101 A | 1/1990 | Cheung et al. | 128/633 |
| 5,069,214 A | 12/1991 | Samaras et al. | 128/633 |
| 5,490,523 A | 2/1996 | Isaacson et al. | 128/633 |
| 5,635,726 A | 6/1997 | Zavislan et al. | 350/559.44 |
| 5,746,697 A | 5/1998 | Swedlow et al. | 600/323 |
| 5,924,979 A | 7/1999 | Swedlow et al. | 600/300 |
| 6,354,710 B1 | 3/2002 | Nacouzi | 362/96 |
| 6,409,662 B1 * | 6/2002 | Lloyd et al. | 600/300 |
| 6,584,336 B1 * | 6/2003 | Ali et al. | 600/323 |
| 6,591,123 B2 * | 7/2003 | Fein et al. | 600/323 |
| 6,600,940 B1 * | 7/2003 | Fein et al. | 600/323 |
| 6,675,031 B1 * | 1/2004 | Porges et al. | 600/322 |

FOREIGN PATENT DOCUMENTS

| | | | |
|---|---|---|---|
| DE | 4031288 C1 | 10/1990 | |
| DE | 4322139 A1 | 1/1994 | |
| DE | 4420182 A1 | 6/1994 | |
| DE | 19533103 A1 | 3/1996 | |
| DE | 19537876 A1 | 4/1996 | |
| DE | 19626101 A1 | 1/1997 | |
| DE | 19713935 A1 | 10/1997 | |
| EP | 0102816 | 3/1984 | A61B/5/02 |
| EP | 0508526 A1 | 10/1992 | |
| EP | 0615403 A2 | 9/1994 | |
| EP | 0684755 A1 | 11/1995 | |
| EP | 0762809 A2 | 3/1997 | |
| FR | 2686762 | 1/1992 | |

(List continued on next page.)

*Primary Examiner*—Haissa Philogene
(74) *Attorney, Agent, or Firm*—Jack Schwartz and Associates

(57) ABSTRACT

A system and method for adjusting power employed by a light emitting device used for medical applications, such as measurement of patient parameter. A system or device includes a light emitting device, a power unit coupled to the light emitting device for powering the light emitting device and responsive to a control signal for adjusting power applied to the light emitting device, and a control unit for providing the control signal and coupled to the power unit, the control signal being determined in response to a characteristic of a signal associated with a physiological parameter measured using light produced by the light emitting device.

23 Claims, 3 Drawing Sheets

FOREIGN PATENT DOCUMENTS

| | | |
|---|---|---|
| FR | A-2 686 762 | 1/1992 |
| FR | 2738682 | 9/1995 |
| GB | 2292843 A | 3/1996 |
| WO | WO 88/09108 | 11/1988 |
| WO | WO 92/10920 | 6/1992 |
| WO | WO 96/27277 | 9/1996 |
| WO | 9963883 | 12/1999 ............ A61B/5/00 |
| WO | 0061000 | 10/2000 ............ A61B/5/00 |

* cited by examiner

POWER CONSERVING ADAPTIVE CONTROL SYSTEM FOR GENERATING SIGNAL IN PORTABLE MEDICAL DEVICES

CROSS REFERENCE TO RELATED APPLICATION

This patent application is related to and claims benefit of priority from U.S. Provisional Patent Application Ser. No. 60/363,791 filed Mar. 13, 2002 by Johnnie W. Huang et al.

FIELD OF THE INVENTION

The present invention relates to a method and apparatus for controlling and reducing the level of power consumption in medical devices and, in particular, for controlling and reducing the level of power consumption in medical devices, such as blood oximetry devices, employing transmitted or reflected signals or both in combination to measure biological or environmental parameters of a patient or to communicate information pertaining thereto.

BACKGROUND OF THE INVENTION

The medical field commonly employs a wide range of devices that depend upon the transmission of signals to monitor or measure various biological or environmental parameters of a patient. The signals may be transmitted and measurements made of the signal as reflected from or transmitted through, for example, tissue or an organ, or the signal may be used to communicate measured data rather than to obtain the data.

For example, a common example of devices that employ the transmission and reception of signals in the measurement of one or more biological or environmental parameters of a patient are the various forms of blood oximetry devices. As is well known, blood oximetry devices are commonly used to monitor or measure the oxygen saturation levels of blood in a body organ or tissues, including blood vessels, or the oxidative metabolism of tissues or organ. Such devices are often capable of and are used to determine pulse rate and volume of blood flow in organs or tissues, or to monitor or measure other biological or environmental parameters.

Blood oximetry devices may be considered as exemplary medical devices using the transmission or reflection of signals to gain or communication information, and as fairly illustrative of the problems of the prior art.

As is well known to those of skill in the arts, blood oximetry devices measure the levels of the components of one or more signals of one of more frequencies as transmitted through or reflected from tissue or an organ to determine one or more biological or environmental parameters, such as blood oxygenation level and blood volume or pulse rate of a patient. Blood oximetry devices may also be constructed as directly connected devices, that is, devices that are directly connected to a patient and that directly present the desired information or directly record the information. It is also well understood, however, that blood oximetry devices may also be implemented as remote devices, that is, devices attached to or implanted in a patient and transmitting the measurements to a remote display, monitoring or data collection device.

Considering blood oximetry devices in further detail as representative and exemplary of a wide range of medical devices, oximetry devices measure blood oxygen levels, pulse rate and volume of blood flow by emitting radiation in a frequency range, such as the red or near infrared range, wherein the transmission of the radiation through or reflectance of the radiation from the tissues or organ is measurably affected by the oxygen saturation levels and volume of the blood in the tissues or organ. A measurement of the signal level transmitted through a tissue or organ or reflected from a tissue or organ may then provide a measurement or indication of the oxygen saturation level in the tissue or organ.

The transmitted or reflected signals may be of different frequencies which are typically affected in measurably different ways or amounts by various parameters or factors or components of the blood. The conjunctive use of signals at different frequencies, which may be close in frequency, or wavelength, may in turn provide concurrent representations of multiple factors or parameters which may be very different from one another which may be closely related, such as the level of oxygen in the blood in conjunction and a reference for the blood oxygen level measurement. It should also be noted that the parameters or factors represented by transmitted or reflected signals may be represented by different and related or unrelated parameters of the received signals. For example, a signal transmitted through or reflected from tissue or an organ to measure, for example, blood oxygenation or flow, may have a constant or "dc" component due to the steady state volume of blood in the tissue or organ and a time varying or "ac" component indicative of the time varying volume of blood flowing through the tissue or organ due to the heart beat of the body. Each signal component may provide different information, and may provide information that may be used together to generate or determine yet other information.

An example of an oximetry device is described in U.S. Pat. No. 4,281,645 to Jobsis for METHOD AND APPARATUS FOR MONITORING METABOLISM IN BODY ORGANS, which describes an oximetry system which continuously measures the oxidative metabolism of an organ by transmitting alternating reference and measurement light signals through the organ. The device adjusts the power level, or gain, of the receiving photomultiplier to maintain the output signal level generated by the photomultiplier during the reference signal transmission at a predetermined level, and then maintains this amplifier gain level during transmission of the measurement signal. The result is that the photomultiplier gain is automatically compensated for changes in blood volume in the organ, and the amplifier gain control signal reflects and is used as a measurement of blood volume in the organ.

In yet another example, U.S. Pat. No. 4,653,498 to New, Jr. et al. for PULSE OXIMETER MONITOR, describes a pulse oximeter system wherein the power levels of the diodes emitting a reference signal and a measurement signal are adjusted, by measurement of the received reference signal, to provide received signals within the acceptable input voltage range of a digital to analog converter that converts the received signals into measurement indications.

In a further example, U.S. Pat. No. 4,859,057 to Taylor et al. for OXIMETER APPARATUS describes a reflectance oximetry apparatus which transmits a red signal and an infrared signal and determines the dc and pulsating components of the reflected return signals wherein the pulsating component represents the level of blood oxygen. The emitted power of the red and infrared LEDs are controlled to provide a relatively stable level of dc component.

U.S. Pat. No. 5,069,214 to Samaras et al. for FLASH REFLECTANCE OXIMETER describes a flash reflectance oximeter that employs short duration, high intensity red and infrared measurement and reference pulses to allow oximetric measurements through barriers such as clothing or protective wraps. The duration and intensity of the pulses are adjustable by the user to accommodate different thicknesses of material.

In final examples, U.S. Pat. Nos. 5,924,979 and 5,746,697 to Swedlow et al. for MEDICAL DIAGNOSTIC APPARATUS WITH SLEEP MODE describe a medical diagnostic apparatus wherein the apparatus enters a "sleep mode" to conserve power when monitored physiological parameters have been stable and within a selected range for a predetermined period, and are "awakened" for further measurements after selected periods.

The use of yet other devices or systems that rely upon the transmission and reception of some form of signal or signals to detect, monitor or measure yet other biological or environmental parameters of a patient are also well known to those of skill in the arts. For example, many other types of biological or environmental parameter monitoring or measuring device or systems use signals transmitted or reflected through or from tissue or an organ to detect and measure various biological or environmental parameters or may transmit biological or environmental data from a data collection or monitoring device, such as an implanted or remote cardiac monitor, to a data collection device or system. Still other devices or systems, such as an implanted or remote blood oximetry device, may employ transmitted or reflected signals to measure a biological or environmental parameter, such as blood oxygen level, and yet other signals to communicate the information to a remote data receiving device or site. The adaptation of and advantages of the present invention to and in such devices will, however, be well understood by those of skill in the arts.

More recent developments in medical devices, and in particular in medical monitoring and parameter measuring and data collection or monitoring devices, such as blood oximeters, has been in the direction of smaller, lighter and more portable devices. Such "miniaturized" devices may be used, for example, for remote or portable use, such as by emergency response teams, or as individual user devices rather than as devices shared among several users, and are generally more convenient even in a hospital setting as requiring less room for storage and less space when in use. An accompanying trend has been for the combination of two or more devices of different types, which are typically related in some way in function or in use, into a single devices. Yet another trend in recently developed devices is the provision of increased data or signal processing power and data storage capacity, such as required for advanced algorithmic processing.

The development of such smaller and more portable devices, however, has meant greater reliance on smaller, more portable or more convenient power sources to drive the devices, such as batteries as opposed to connections to power lines. This trend, in turn, has led to greater concerns regarding power consumption and battery life of the devices. For example, in a typical blood oximetry device or system, up to 50% or more of the power consumption of the device is used in driving the light sources, which are typically light emitting diodes (LEDs) generating the red or infrared signals that are transmitted through or reflected from the tissue or organ to measure the levels of oxygen in the tissue or organ.

It will be apparent from the above examples of blood oximetry devices, however, that power consumption has not, until recently, been a concern in the design of most medical devices, including blood oximetry devices. For example, It will be noted from the above examples of blood oximetry devices that the oximetry devices of the prior art are, in general, designed to control either the signal level of the transmitted light or the amplification or gain of the receiving circuits so as to provide a received signal of sufficient amplitude and signal to noise ratio to support an analysis providing an acceptably high confidence level. As described in the above cited example, the oximetry devices of the prior art are thereby directed towards increasing the received signal level by either increasing the transmitted signal level or increasing the gain or amplification of the received signal, both of which increase power consumption of the devices. Yet other devices and systems, including those relying upon the transmission and reception of signals for data communication are likewise designed and optimized to increase the received signal level and the received signal "signal to noise" ratio.

There has been some development, however, in providing more efficient LEDs, such as the OxiMax sensors available from Nellcor, that provide the higher levels of brightness for equal or lower power consumption, or in approaches such as that discussed in Swedlow '979 and '697, wherein the device is "put to sleep" for periods predicted on the period or rate of possible change of the measured parameter. LEDs, however, are not suitable or usable for all devices, and may not be able to generate light signals are the desired wavelengths. Also, the method of "putting a device to sleep" based upon a predicted "safe period" before change of a parameter will not be acceptable in all instances. In many instances, continuous monitoring will be necessary or desirable due to the significance of the parameter being measured or monitored or the risks represented or reflected in the parameter or, in some instances, the period or rate of change of the parameter may be unpredictable or too short to allow a "sleep" period. Yet other approaches of the prior art for power reduction include reducing the level of the emitted signal, as is suggested for other reasons in Samaras '214. It must be noted, however, that such power reductions are, as in Samaras '214, typically for other reasons, such as avoiding burning the patient, and that such methods are risky or unacceptable because a reduction of emitted signal power may result in the desired information in the signal becoming buried in environmental and system noise, or being degraded to the point of being useless or even hazardous.

SUMMARY OF THE INVENTION

The present invention is directed to a system and method for adjusting power employed by a light emitting device used for medical applications, such as measurement of patient parameter. A system or device of the present invention includes a light emitting device, a power unit coupled to said light emitting device for powering the light emitting device and responsive to a control signal for adjusting power applied to the light emitting device, and a control unit for providing the control signal and coupled to the power unit, the control signal being determined in response to a characteristic of a signal associated with a physiological parameter measured using light produced by the light emitting device.

BRIEF DESCRIPTION OF THE DRAWINGS

The invention will now be described, by way of example, with reference to the accompanying drawings in which.

DESCRIPTION OF THE PREFERRED EMBODIMENT(S)

Figure 1:
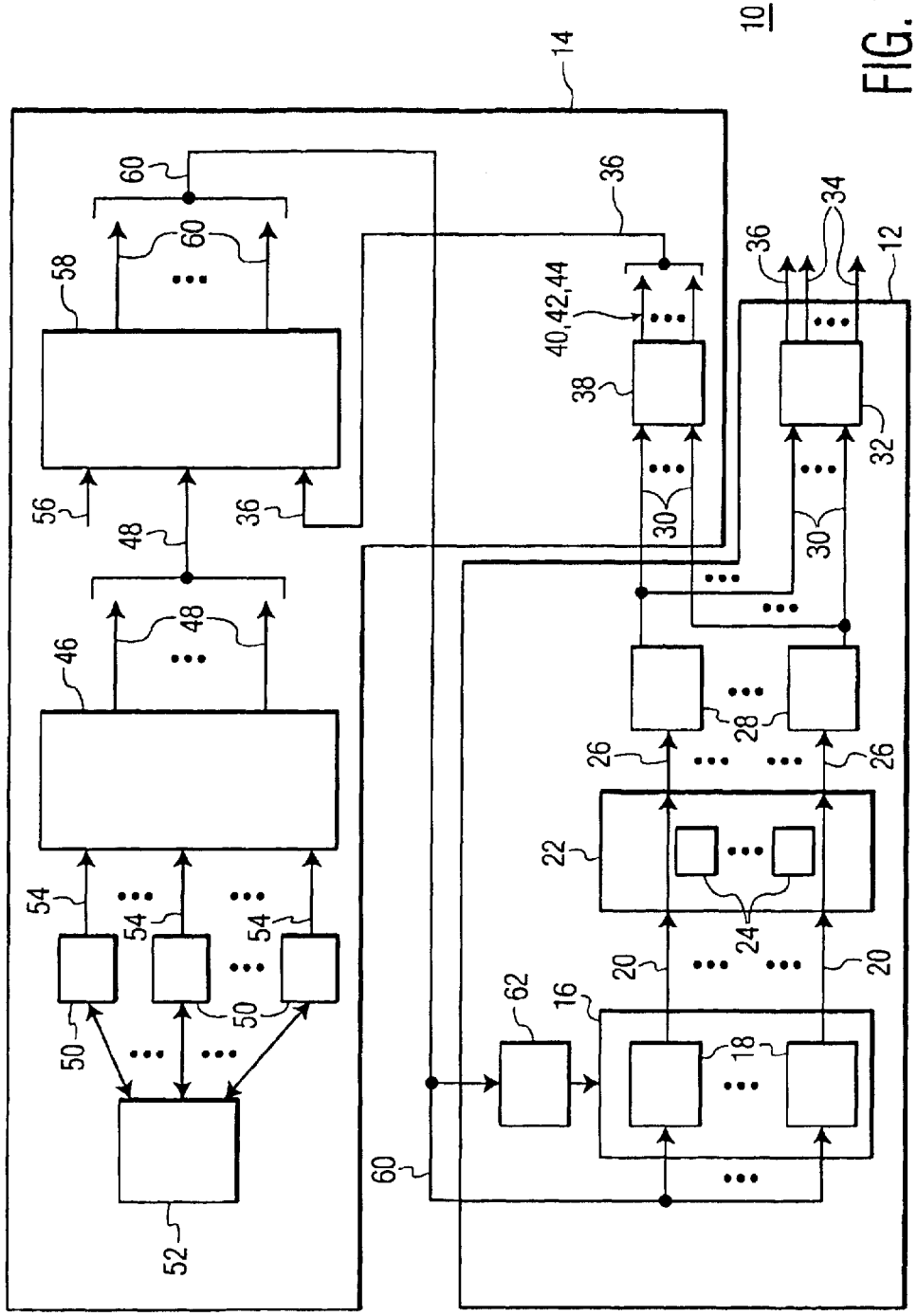
FIG. 1 is a is a diagrammatic representation of a device for monitoring a patient parameter and an emitted signal controller for controlling a signal characteristic of an emitted parameter monitoring signal.

Referring to FIG. 1, therein is shown a diagrammatic representation of a Device 10 using one or more signals transmitted through or reflected from tissue or an organ to measure or monitor a parameter of the tissue or the organ and in which the present invention may be implemented. As discussed herein above, an example of such a Device 10 may be a blood oximetry device, and a Device 10 may be a self contained device or may be a part of a larger system that may include a plurality of Devices 10 of different types.

As illustrated in FIG. 1, a Device 10 will include a Parameter Measurement Unit 12 for making measurements of one or more parameters of the tissue or organ, typically and in the present invention by measuring light transmitted through or reflected from the tissue or organ. According to the present invention, a Emitted Signal Power Control Unit 14 is associated with the Parameter Measurement Unit 12, either as a part of the Device 10 or as a separate but associated unit, and monitors and controls the power levels of the signals emitted by the Parameter Measurement Unit 12.

A typical Device 10 will include a Signal Source 16 which contains one or more Signal Emitters 18 for generating corresponding Emitted Signals 20. Emitted Signals 20 are transmitted through or reflected from a Parameter Target 22, which may be comprised of tissue, an organ or any other type of body part or biological entity having Parameters 24 which are to be measured or monitored. The Emitted Signals 20 that are transmitted through or reflected from the Parameter Target 22 are received as Modulated Signals 26 by Sensors 28 wherein the components or characteristics of Modulated Signals 26 have been modulated or otherwise modified from the original Emitted Signals 20 by the Parameters 24 and other characteristics of Parameter Target 22. Sensors 28 in turn provide Received Signals 30 that correspond to and represent Modulated Signals 26 and the components and characteristics of Modulated Signals 26 due to modulations and modifications imposed on or induced in Emitted Signals 20 due to Parameters 24.

Modulated Signals 26 and Received Signals 30 thereby contain information relating to Parameters 24 of the Parameter Target 22, and that information can be extracted or otherwise obtained from Received Signals 30 by appropriate signal processing. Such processing may include, for example, comparing components of Modulated Signals 26, as represented by Received Signals 30, with those of Emitted Signals 20 or detecting and extracting components of Received Signals 30, such as the "dc" and "ac" components of the signal or signals. The processing of Received Signals 30 to obtain the desired information comprising or pertaining to Parameters 24 is performed by a Parameter Signal Processor 32, which provides Parameter Outputs 34, which in turn represent Parameters 24 and which may be displayed, stored for later display or subsequent processing, or transmitted to another facility or system.

The specific process and algorithms by which Received Signals 30 are processed to generate Parameter Outputs 34 representing the desired information regarding Parameters 24, and the number, frequencies, waveforms and other characteristics of Signal Emitters 18, Emitted Signals 20, Modulated Signals 26, Sensors 28, and Received Signals 30 and so on, are dependent upon the specific Parameters 24 and Parameter Targets 22 of interest. These factors, elements and processes are, however, well known to and understood by those of skill in the relevant arts and the adaptation of the present invention to different ones and different combinations of these factors, elements and processes will be well understood by those of skill in the relevant arts. As such, these elements need not and will not be discussed in further detail herein.

It has been discussed herein above that a significant potential reduction in power consumption of a Device 10 could be realized by reduction in the emitted power levels of Emitted Signals 20 as the power consumed by Signal Emitters 18 often comprise 50% or even more of the power consumed by the Device 10. As has been discussed, however, the desired information in the signal may become buried in environmental and system noise or may otherwise may become degraded or distorted to the point of being useless or hazardous.

According to the present invention, however, the emitted power levels of Emitted Signals 20 may be reduced from their maximum or normal levels to some intermediate or relatively lower level so long as the "quality" of the signal components of interest of the corresponding received Modulated Signals 26 and Received Signals 30 are such that the Parameter Outputs 34 may be extracted or otherwise obtained from the signal or signals with a level of reliability and a confidence level that is acceptable for purposes of the measurement or monitoring process. In this respect, and for purposes of the present invention, the "quality" of a given signal or the components of a signal are determined by signal characteristics such as the signal power level, amplitude or "intensity", or "signal to noise ratio", which may be a ratio between the signal and noise from various sources, the ratio of a signal component to noise in the signal, or a ratio between components of the signal. Other exemplary signal characteristics pertaining to the "quality" of a signal may include the waveform or frequency of the signal, that is, does the waveform or frequency of the signal as received correspond or correlate to a sufficient degree with the waveform or frequency of the signal as transmitted, and so on.

For purposes of the following descriptions, the term "received" signal characteristics or characteristic of a Received Signal 30 and/or the corresponding Modulated Signal 26 will generally refer to those factors of the signal itself, such as received power levels, ratios of signal components to noise, and so on, that will determine the probability that a Parameter Output 34 may be extracted or otherwise obtained from the signal or the components thereof with a level of reliability and a confidence level that is acceptable for the intended purposes. The term "required" signal characteristic or characteristics, in turn, will refer to the characteristics of a signal, that is, a Received Signal 30 or the corresponding Modulated Signal 26, that are required and necessary to provide an acceptable probability that a Parameter Output 34 may be extracted or otherwise obtained from the signal or the components thereof with a level of reliability and a confidence level that is acceptable for the intended purposes. Comparison of the received signal characteristics of a Received Signal 30 or the corresponding Modulated Signal 26 with the required signal characteristics of the Received Signal 30 or corresponding Modulated Signal 26 will thereby indicate the probability that a Parameter Output 34 may be extracted or otherwise obtained from the Received Signal 30 and corresponding Modulated Signal 26 with a level of reliability and a confidence level that is acceptable for the intended purposes To illustrate by example, the signal characteristic of interest for generating a Parameter Output 34 may be the signal to noise ratio of a component of the Received Signal 30 and corresponding Modulated Signal 26, and the "received" signal characteristic, that is, the signal to noise ratio as received at the sensor, may be 2 db. The "required" signal characteristic, however, may be a signal to noise ratio of 3 db in order to generate the desired Parameter Output 34 with an acceptable degree of reliability and an acceptable confidence level. A Received Signal 30 having a signal to noise ratio of 2 db will thereby be of relatively low "quality" as the probability that the Parameter Output 34 will be generated from the signal with the required levels of reliability and confidence will be relatively low. If, however, the Received Signal 30 characteristic were 4 db, the signal would be of relative high "quality" as the probability that the Parameter Output 34 could be generated with the required degree of reliability and level of confidence would be relatively high. In this latter instance, therefore it may be possible for the Device 10 to reduce the emitted power level of the corresponding Emitted Signal 20, thereby reducing the power consumption of the Device 10 accordingly.

Expressed in terms of signal "quality", therefore, it may therefore be said that the "required quality" of a signal is represented by the minimum values of signal characteristics, such as signal amplitude or signal to noise level, that must be possessed by the signal to provide the necessary probability of obtaining the Parameter 24 with the required reliability and confidence level. The "quality" of the signal, in turn, is a measure of the degree to which the received signal characteristics of the signal meet the required signal characteristics.

The present invention recognizes that the required signal characteristics of Modulated Signals 26 for purposes of providing Parameter Outputs 34 with the required level of confidence are not solely dependent upon either the power levels of Emitted Signals 20 or of the corresponding Modulated Signals 26. Instead, and according to the present invention, the required signal characteristics of Modulated Signals 26 for the purposes generating Parameter Outputs 34 is dependent upon and determined by a number of factors, which may be generally classified as inherent signal factors and environmental factors.

Inherent signal factors pertain and relate to the received signal characteristics of Modulated Signals 26 in themselves, and thus the signal characteristics of Received Signals 30, and, in particular, to whether the received signal characteristics of the Modulated Signals 26 as represented by Received Signals 30 are such that Parameter Outputs 34 may be generated or extracted from Received Signals 30 with the required degree of reliability and level of confidence. As discussed herein above, the received signal characteristics used in generating Parameter Outputs 34 may include, for example, signal power level, amplitude or "intensity", "signal to noise ratio", wherein the "noise" may be any other signal component, the waveform or frequency of the signal and any distortion or modification thereof, and so on. Inherent signal factors thereby include such factors as the characteristics of Signal Emitters 18, Parameters 24, Sensors 28 and the processing operations of Parameter Processor 32, and so on.

"Environmental" factors, in turn, relate to factors, such as patient condition, that to various degrees determine the "required" signal characteristics of the Modulated Signals 26, that is, the signal characteristics that the Modulated Signals 26 are required to possess in order to allow Parameter Outputs 34 to be obtained from Received Signals 30 with the necessary degree of reliability and level of confidence. For example, if a patient is in or has a condition that represents a heightened medical risk, it may be necessary to determine and monitor a given related Parameter 24 to a higher level of accuracy and confidence and with a lower possibility of error in order to adequately monitor the patient. The necessary levels of confidence and accuracy may in turn impose a higher level of required signal characteristic or characteristics in order to appropriately increase the probability that the measurement of the Parameter 24 and the corresponding Parameter Output 34 will be obtained with the necessary increased degree of reliability and level of confidence.

In blood oximetry, for example, a base requirement is that the received signal level of the Modulated Signal 26 and thus the emitted signal level of the corresponding Emitted Signal 20 must be sufficient to allow the calculation of saturated oxygen pressure (SPO2) of the blood and pulse rate (PLS) with the necessary degree of accuracy and reliability. If the patient stability has deteriorated, however, which may be indicated by changes in the base level of SPO2 and PLS, progressive lowering of SPO2, the rate of change of PLS, instability in SPO2 and PLS, the received signal characteristics of Modulated Signals 26 must be increased or improved accordingly to insure an adequate and safe level of monitoring of the patient.

In summary, therefore, environmental factors may be defined as factors effecting and determining the required signal characteristics of Modulated Signals 26 and the corresponding Received Signals 30 to insure that Parameters 24 may be determined to the required level of confidence. Inherent signal factors, in turn, determine whether the Modulated Signals 26 in fact possess received signal characteristics that meet or exceed the required signal characteristics. Stated another way, signal environment factors determine, at least in part, the standards that must be met by a Modulated Signal 26 and thus by the Received Signal 30, while the received signal characteristic factors determine whether the Modulated Signal 26 and corresponding Received Signal 30 and meet those standards.

The present invention recognizes that the received signal characteristics of Modulated Signals 26 and Received Signals 30 will typically contain both Parameter 24 related information that may be used in generating Parameter Outputs 34 and information reflecting the "quality" of the Modulated Signal 26 signal components, and thus of the Received Signal 30 components from which the Parameter Outputs 34 are generated. In this respect, it must again be repeated that the term "quality" refers to the received signal characteristics of a Modulated Signal 26 and the corresponding Received Signal 30 that determine whether one or more Parameter Outputs 34 may be obtained from the Modulated Signal 26 with an acceptable level of confidence for the purposes intended.

For example, in blood oximetry the desired Parameter 24 information typically relates to the static and dynamic volume of blood in a body of tissue, which will typically be measured by a beam of light passing through the tissue and wherein the absorption of light by the blood in the path through the tissue will vary according to the volume of blood in the tissue. The Signal Emitter 18 will thereby typically be a Light Emitting Diode (LED) or low power laser, while the Sensor 28 will be some form of photosensitive device. The received signal characteristics of interest in the Modulated Signal 26 and corresponding Received Signal 30 will include a steady state or time invariant, or "dc", component, such as a component due to the steady state volume of blood in a tissue or organ, a time varying or "ac" component indicative of the varying volume of blood flowing through the tissue or organ, and a "noise" component arising from various sources. The information sought to be extracted from the Modulated Signal 26 and Received Signal 30 for generating a Parameter Output 34 representing the oxygen saturation levels of blood in a body organ or tissues is thereby primarily the "ac" component of the signal, which is indicative of the varying volume of blood flowing through the tissue or organ. As such, either or both of the "dc" and "noise" components are either of less interest for these purposes or may interfere with the extraction of the information of interest. The amplitude or signal strength of the "ac" component is thereby representative of the Parameter 24, that is, the oxygen saturation level, while the ratio of the amplitude of the "ac" component relative to other signal components, that is, the signal to noise ratio of the "ac" component, is pertinent to the "quality" of the Modulated Signal 26 and Received Signal 30.

As described, therefore, Parameter Processor 32 will extract information pertaining to a Parameter 24 from the signal characteristics of a Received Signal 30 representing a Modulated Signal 26, and will use or otherwise process the extracted information to generate and provide a corresponding Parameter Output 34.

Parameter Processor 32 may also, however, extract information pertaining to the "quality" of a Received Signal 30 and the corresponding Modulated Signal 26 from the signal characteristics of the Received Signal 30, and may generate one or more Signal Quality Outputs 36 representing "qualities" of the Received Signal 30 and the corresponding Modulated Signal 26. A Signal Quality Processor 38 may also extract signal quality information from one or more Received Signals 30, either in addition to or instead of Parameter Processor 32, and may generate one or more corresponding Signal Quality Outputs 36 representing one or more signal qualities of one or more Received Signals 30 and the corresponding Modulated Signals 26. Also, signal quality information extracted by Parameter Processor 32 may be provided to Signal Quality Processor 38 for use in the generation of Signal Quality Outputs 36 by Signal Quality Processor 38.

It will be recognized that there may be a wide range and variety of types of Emitted Signals 20 used to detect Parameters 24 and a wide range and variety of Modulated Signal 26 signal characteristics that may be detected and measured, again depending upon the Parameters 24. There may also be a correspondingly wide range and variety of methods for processing the signal characteristics of the Modulated Signals 26 and Received Signals 30 that contain the information representing a Parameter 24 to provide Parameter Outputs 34. It will, therefore, also be recognized that the signal characteristics of a Received Signal 30 that are processed by Parameter Processor 32 will depend upon a given Parameter 24 and upon the corresponding form and characteristics of the corresponding Emitted Signal 20, Modulated Signal 22 and Sensor 28. The types of Parameters 24, the types of Emitted Signals 20 and the types of signal characteristics that may exist and be processed to generate Parameter Outputs 34, however, will in general be well known to those of ordinary skill in the arts and need not be discussed in further detail herein.

Referring again to Signal Quality Processor 38, as shown Signal Quality Processor 38 receives Received Signals 30 in the same manner as Parameter Processor 32, and generates one or more Signal Quality Outputs 36 wherein each Signal Quality Output 36 is a value generated from one or more received signal characteristics of one or more Received Signal 30 signal components representing the "quality" of a Modulated Signal 26. As just discussed, one or more Signal Quality Outputs 36 or information for generating Signal Quality Outputs 36 may also be generated or provided by Parameter Processor 32.

It will be recognized that there may be a wide variety of possible Signal Quality Outputs 36, depending on the Device 10, the Parameters 24 of interest, the type and nature and of Modulated Signals 26 and the signal characteristics of the Modulated Signals 26, and so on. In addition, the Signal Quality Outputs 36 representing various aspects of the "quality" of Modulated Signals 26 and the components thereof may be generated or extracted in a variety of ways, depending upon the natures of the Modulated Signals 26 and Received Signals 30 and the information to be extracted from the Received Signals 30.

For example, the Signal Quality 36 outputs may include a Modulation Index 40 that represents a modulation level of a Modulated Signal 26, that is, a ratio between an "ac" component and a "dc" component of the signal or a ratio between two "ac" components of the signal or a ratio between the components of two or more signals. The Modulation Index 40 will thereby generally reflect, for example, the ratio of the information component of the signal to the undesired signal components of the signal, including noise. It will also be recognized that the Modulation Index 40 may also provide information that may be used in generating a Parameter Output 34, as well as representing the "quality" of the signal or signal components.

Yet another Signal Quality 36 output may be an Intensity Index 42I, which will generally represent the intensity, level, magnitude or power level of a Modulated Signal 22 or a signal component thereof as received by a corresponding Sensor 28. The Intensity Index 42 thereby represents the received signal amplitude, which may be used in determining whether the amplitude of the signal or signal component is adequate for the signal to be received, detected and processed to provide the Parameter 24 with an acceptable level of confidence. Again, an Intensity Index 42 value may be used in generating a Parameter Output 34, as well as determining the quality of the signal from which the Parameter Output 34 is generated.

Still another possible Signal Quality 30Q output is a Signal Quality Index 44, which may be generated by correlating a Modulated Signal 22 or Received Signal 30 or a component thereof with itself, with its corresponding Emitted Signal 20 or with another signal generated for the purpose. A Signal Quality Index 44 may be normalized by scaling the correlation results with the amplitude of a component of the signal or signals, and the scaling may be performed during the correlation or upon the results of the correlation. A Signal Quality Index 44 thereby represents, for example, whether the signal has been distorted or otherwise modified in the path between its emission and its reception, and the nature and degree of the change in the signal, and will often provide information that may be used in generating a Parameter Output 34.

Yet other Signal Quality 36 outputs may represent other measures of the received signal characteristics of a Modulated Signal 22 or Received Signal 30 or a component thereof, many of which will be well known to and recognized by those of ordinary skill in the relevant arts. For example, certain Signal Quality 36 outputs may represent one or more "signal to noise" ratios measured between components of a Modulated Signal 22 or Received Signal 30, and so on.

As in the instance of Parameter Processor 32, it will be recognized that there may be a wide range and variety of types of Emitted Signals 20 to detect the Parameters 24 and a wide range and variety of Modulated Signal 26 or Received Signal 30 signal characteristics that may be detected and measured to determine signal quality, and a correspondingly wide range and variety Signal Quality Outputs 36 and of methods for processing the signal characteristics of a Received Signal 30 to generate Signal Quality Outputs 36. It will also be recognized that the signal characteristics of a Received Signal 30 that are processed by Signal Quality Processor 38 will depend upon a given Parameter 24, the corresponding form and characteristics of the corresponding Emitted Signal 20 and Modulated Signal 26, and the nature and form of the desired Signal Quality Output 36. The types of Parameters 24, the types of Emitted Signals 20 and the types of signal characteristics that may exist and the methods for processing the signal characteristics to generate Signal Quality Outputs 36, however, will in general be well known to those of ordinary skill in the arts and need not be discussed in further detail herein.

Lastly, it will be recognized that the operations and functions of Parameter Processor 32 and Signal Quality Processor 38 may overlap in whole or in part in many instances, such as in the signal characteristics that are processed to obtain Parameter Outputs 34 and Signal Quality Outputs 36 and the methods used in processing the signal characteristics. It will therefore be recognized that, for these reasons, at least certain elements and mechanisms of Parameter Processor 32 and Signal Quality Processor 38 may be shared or integrated and that, in at least some instances, Parameter Processor 32 and Signal Quality Processor 38 may comprise a single processing unit.

Next considering environmental factors, as discussed above environmental factors relate to and affect the level of quality required of a Modulated Signal 26, that is, they determine the required signal characteristics of the Modulated Signal 26 in order to generate a Parameter Output 34 with the required level of confidence. For these reasons and purposes, a Device 10 of the present invention may thereby further include a one or more Environmental Processors 46 generating one or more Environment Outputs 48. Each Environment Output 48 pertains to the environment or conditions under which the Device 10 is operating and may be used to determine, at least in part, the required signal characteristics of a Modulated Signal 26. That is, Environment Outputs 48 do not directly reflect the "quality" of a Modulated Signal 26, but instead reflect or represent factors, such as patient conditions, that determine the level of "quality" required of a Modulated Signal 26 for the intended purposes of the Modulated Signal 26.

Associated with Environmental Processor 46 are one or more Environmental Sensors 50 for sensing Environmental Conditions 52 and providing corresponding Environmental Signals 54 measuring or otherwise representing the Environmental Conditions 52 to an Environmental Processor 46. As described, each Environmental Processor 46, in turn, generates one or more Environment Outputs 48 that represent modifications that may or should be made in the required signal characteristics of one or more Modulated Signals 26. As has been discussed, certain patient conditions may recommend an increase in the required signal characteristics of one or more Modulated Signals 26 in order to increase the level of monitoring of the patient. Other conditions may allow required signal characteristics to be reduced, such as signal power, thereby reducing the power consumption of the Device 10. In this regard, it must be noted that the sensing of a single Environmental Condition 52 may not provide sufficient information to determine required or allowed modifications to the required signal characteristics of a given Modulated Signal 26. For this reason, the presently preferred embodiment measures or senses a collective of Environmental Conditions 52 to provide sufficient information for the intended purposes.

As described, the Environmental Conditions 52 monitored by Environmental Sensors 50 and reflected in Environment Outputs 48 may include factors pertaining to the transmission and reception of Modulated Signals 26, that is, factors affecting the transmission path between Signal Emitters 18 and Sensors 28. In particular, however, the Environmental Conditions 52 sensed by Environmental Sensors 50 and represented by the Environment Outputs 48 will include physical characteristics, conditions or factors related to a patient that are of interest and relevance with respect to determining Parameters 24. For example, Environmental Sensors 50 and Environment Outputs 48 may detect and represent a pulse rate, a change in the pulse rate, a patient temperature, a patient blood pressure, a respiration rate of, for example, exhaled $CO_2$ levels, a hematocrit level, or a cardiac index by means of corresponding appropriate Environmental Sensors 50. Other Environmental Conditions 52 may include, for example, levels and orientations of electric and magnetic fields during various imaging processes, and so on. Others of Environmental Conditions 52 and Environmental Outputs 48 may comprised, for example, of currently measured noise characteristics, previously measured or recorded noise characteristics, predicted noise characteristics or otherwise known noise characteristics of the Device 10, including or any element or component thereof or of a system incorporating the Device 10 It will also be noted that certain of Environment Outputs 48 may also be employed as or in generating certain of Parameter Outputs 34, or in correcting or compensating the Parameter Output 34 values generated by Parameter Processor 32 for the effects of environmental conditions.

A Device 10 may include or be associated with one or a plurality of Environmental Processors 46, and one or more Environmental Processors 36 and Environmental Sensors 50 may be integral with the Device 10 while others may be separate or independent devices. For example, a blood oximetry Device 10 may include integral Environmental Sensors 50 and the appropriate Environmental Processor 46 circuitry for measuring patient blood pressure, respiration rate or exhaled $CO_2$ levels. The Environmental Sensors 50 and corresponding Environmental Processors 46 for, for example, a hematocrit level or a cardiac index may be separate or independent devices and the Device 10 may be provided with Environmental Outputs 48, or outputs capable of meeting the requirements and functions of Environmental Outputs 48, directly from these devices as normal outputs of the devices. In other instances, the Environmental Outputs 48 may represent previously measured or determined factors, such as previously recorded or measured noise characteristics, and the corresponding Environmental Sensors 50 may not be associated with the Device 10 or a system incorporating the Device 10 at the time the Device 10 is in use It will also be noted that the type and complexity of processing provided for a Environmental Signal 54 from an Environmental Sensor 50 to generate a corresponding Environmental Output 48 will depend upon the environmental condition being sensed and the Environmental Sensor 50 used for that purpose. For example, the Environmental Processor 46 for a given Environmental Sensor 50 may be no more than a buffer or isolation amplifier while in another case the Environmental Processor 46 may be a very complex signal processing device for detecting and monitoring integral with or associated with Device 10 may.

According to the present invention, a Device 10 further includes a Signal Evaluation Processor 58 that evaluates the current signal characteristics of Emitted Signals 20 to determine the reliability, accuracy and level of confidence with which Parameters 24 and being detected and measured. As described, this evaluation is performed on the basis of the received signal characteristics of Modulated Signals 26 and Received Signals 30, as represented by Signal Quality Outputs 36, with comparison to the required signal characteristics of Modulated Signals 26, as represented by Required Signal Characteristics 56, and adjusted by the current environmental conditions, and in particular the patient conditions, as represented by Environmental Outputs 48.

In a blood oximetry Device 10, for example, the Signal Evaluation Processor 58 may receive Signal Quality Outputs 36 including one or more of a Modulation Index 40 and an Intensity Index 42I for the Modulated Signal 26 and Received Signal 30 representing the current SPO2 level. The Signal Evaluation Processor 58 may also receive Signal Quality Outputs 36 that include a Signal Quality Index 44 and one or more measurements of "signal to noise" ratios of the components of the SPO2 Modulated Signal 26 and Received Signal 30. The Required Signal Characteristics 56 in turn will typically include a Required Signal Characteristic 56 for and corresponding to each of the Signal Quality Outputs 36 and indicating the received signal characteristics of the corresponding Modulated Signals 26, as represented by Received Signals 30, that are required for Parameter Outputs 34 to be generated to the required levels of accuracy and reliability and to the necessary level of confidence. Lastly, the Environmental Outputs 48 provided to the Signal Evaluation Processor 58 may include, for example, the patient pulse rate and blood pressure, respiration rate and exhaled $CO_2$ levels, and perhaps a hematocrit level or a cardiac index.

Signal Evaluation Processor 58 will then generate one or more Signal Power Control Signals 60 from the Signal Quality Outputs 36, Required Signal Characteristics 56 and Environmental Outputs 48 according to an algorithm selected to control the emitted power of one or more Emitted Signals 20 to provide the necessary accuracy, reliability and level of confidence required or desired for Parameter Outputs 34 under the current environmental conditions. As indicated in FIG. 1, a Signal Power Control Signal 60 may control the emitted power level of an Emitter 20 directly, or may control a Power Supply 62 providing power to one or more Emitters 20.

In the presently preferred embodiment of the invention, Signal Evaluation Processor 58 will control and adjust the emitted power of one or more Signal Emitters 20 according to whether the received signal characteristics of the corresponding Modulated Signals 26 as represented by the corresponding Received Signals 30 meet, exceed or fail to meet the required signal characteristics for the Modulated Signals 26, as modified for the current patient conditions.

If the evaluation of a Modulated Signal 26 through the corresponding Received Signal 30 indicates that the "quality" of the Modulated Signal 26 exceeds the level required to generate a Parameter Output 34 with the desired level of accuracy, reliability and confidence under the current environmental conditions by more than a predetermined limit, Signal Evaluation Processor 58 may reduce the power level of the corresponding Emitted Signal 20 accordingly until the quality of the Modulated Signal 26 is within an acceptable range of the required level, but is not below that level. The result will thereby be a reduction in the emitted signal power level, and a reduction in the power consumption of the Device 10.

If the evaluation indicates that the quality of the Modulated Signal 26 does not meet the level required to generate the Parameter Output 34 with the desired level of accuracy, reliability or confidence under the current environmental conditions, Signal Evaluation Processor 58 may increase the power level of the corresponding Emitted Signal 20 accordingly until the quality of the Modulated Signal 26 is within an acceptable range of the required level. The result in this case will thereby be an increase in the emitted signal power level and a corresponding increase in the power consumption of the Device 10, but an increase in the accuracy, reliability and confidence with which the Parameter Output 34 is generated.

In either event, the measurement of Parameters 24 will safely meet the levels of reliability, accuracy and confidence required or desired for a given patient, while providing the most efficient use of the power available to the Device 10.

It will be recognized that the evaluation of Modulated Signals 26 may be implemented in a variety of embodiments of the present invention. For example, Signal Evaluation Processor 58 may evaluate the received signal characteristics with respect to the required signal characteristics, and then adjust evaluation according to the current environmental conditions to generate the final output. Alternatively, the Signal Evaluation Processor 58 may adjust the required signal characteristics according to the current environmental conditions, and then evaluate the received signal characteristics according to that result. In yet other embodiments, a Signal Evaluation Processor 58 may perform the signal characteristics adjustments entirely dynamically; that is, "starting from zero" for each new monitoring or measurement of a patient, or may store a set of initial starting signal characteristics, which may be predetermined or historically derived. In yet another embodiment, the initial signal characteristics may be set "by hand", and so on.

It will also be recognized that the methods of the present invention may be used to control a variety of signal characteristics of Emitted Signals 20 and thus of Modulated Signals 26, although the emitted power levels of Emitted Signals 20 will be the factor most often controlled. For example, a Signal Evaluation Processor 58 may alternatively control the frequency, pulse rate, pulse width or waveform of an Emitted Signal 20, rather than the signal power. In other embodiments, it may be advantageous to control the detection of Modulated Signals 26 by, for example, adjustment of the sensitivity or gain of Sensors 28 or the associated circuitry or by providing a range of processes for processing Modulated Signals 26 and Received Signals 30 to obtain the information for generating Parameter Outputs 34, and so on. In all instances, however, the goal of the embodiment will be an increase in efficiency in the use of system power while insuring adequate or improved signal qualities and improved results.

In summary, therefore, the present invention is directed to a method for monitoring a patient parameter or some other biological or physiological or chemical parameter by transmitting a monitoring signal from a signal source and to or through a target wherein the monitored parameter is a characteristic of the target. A modulated signal representing the emitted monitoring signal as modulated by the parameter is received by an appropriate sensor and the monitored parameter is determined from the characteristics of the modulated signal. In the particular, the present invention is directed to a method for controlling a signal characteristic of the emitted monitoring signal to control a characteristics of the emitted monitoring signal, such as the signal power, while insuring that the characteristics of the received modulated signal are such as to allow satisfactory determination of the monitored parameter.

Figure 2:
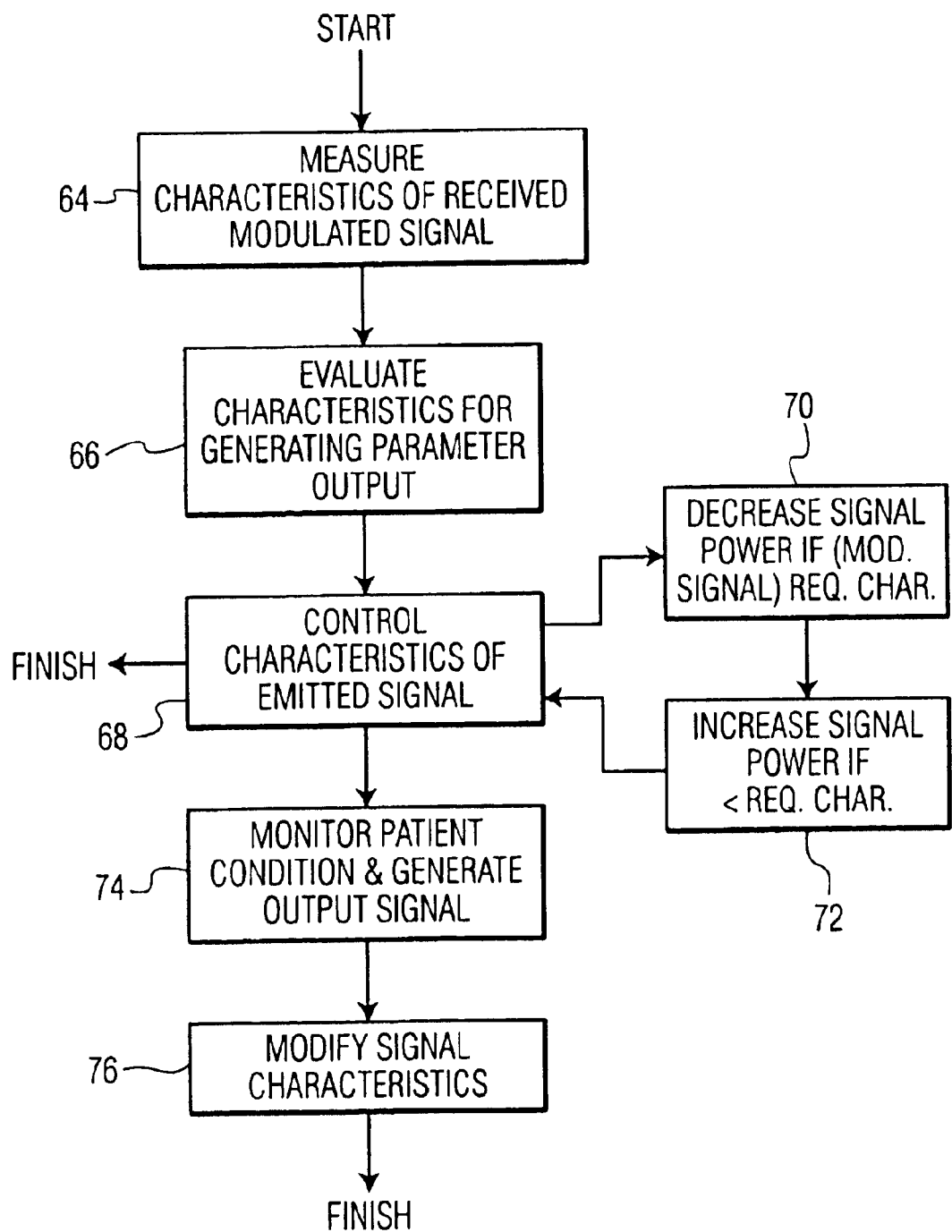
FIG. 2 is a flowchart illustrating the method of the present invention.

According to the present invention, therefore, and as illustrated in FIG. 2, the method of the present invention thereby includes the steps of:

Step 64: measuring received signal characteristics of a modulated signal (26),

Step 66: evaluating the received signal characteristics of the modulated signal (26) with respect to required signal characteristics of the modulated signal (26) for generating a parameter output (34), and Step 68: controlling an emitted signal characteristic of a emitted monitoring signal (16) so that the received modulated signal (26) possesses the required signal characteristics.

Step 68 may then includes the steps of:

Step 70: decreasing the emitted signal (16) power level when the received signal characteristics of the modulated signal (26) exceed the required signal characteristics for generation of the parameter output (34), and Step 72: increasing the emitted signal (16) power level when the received signal characteristics of the modulated signal (26) are lower than the required signal characteristics for generation of the parameter output (34), and in an implementation for monitoring a condition of a patient, the method of the present invention may include the steps of:

Step 74: monitoring a patient condition (52) and generating a corresponding environmental condition output (48) representing an environmental condition (52) of the patient affecting monitoring of the parameter (24), and Step 76: modifying the required signal characteristics of the modulated signal (26) according to the monitored patient environmental condition (52).

Figure 3:
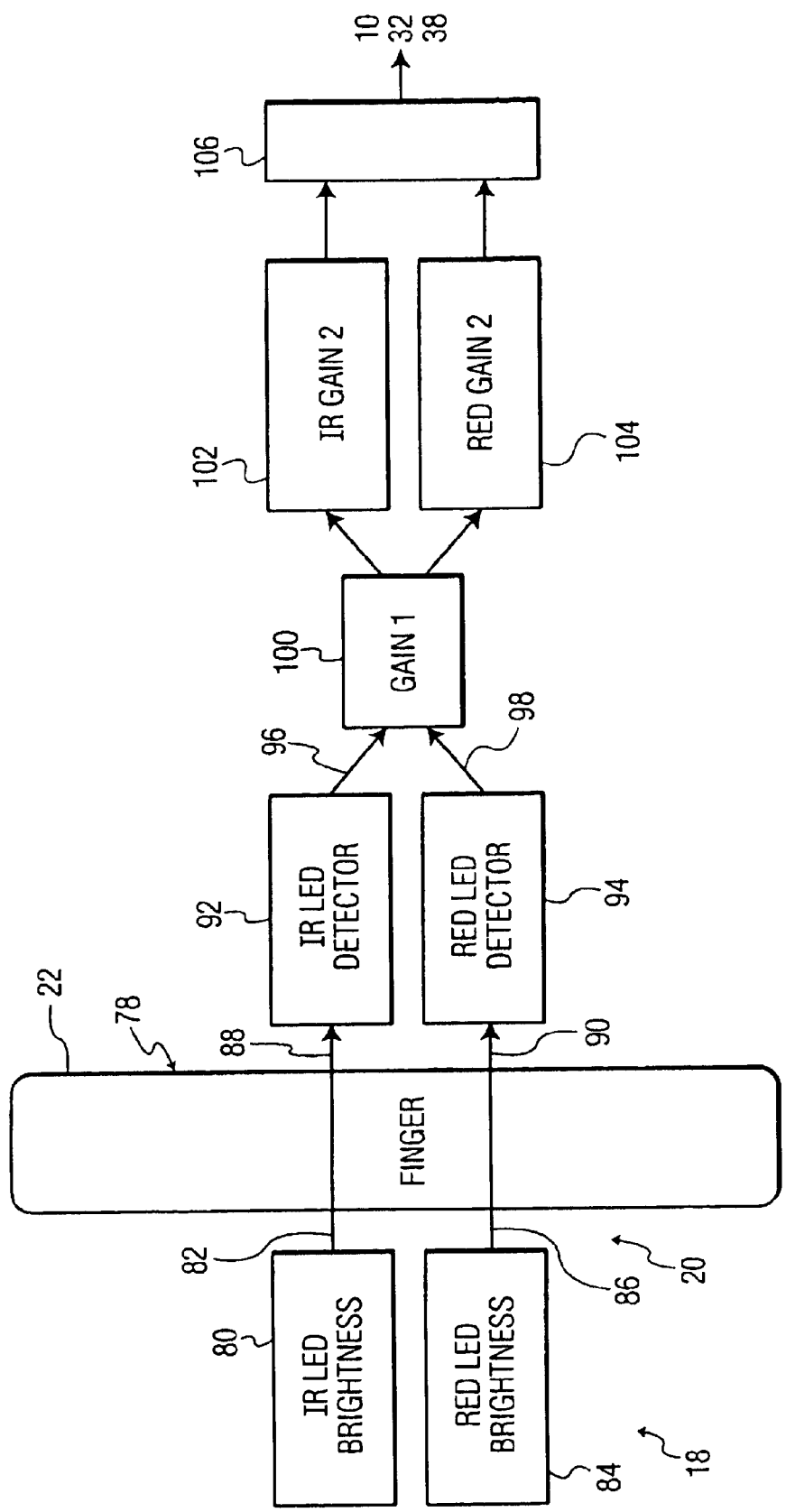
FIG. 3 illustrates an example of the operation of the present invention.

Finally, FIG. 3 illustrates an example of the operation of the present invention as embodied for a pulse oximetry $SpO_2$ system in which Emitted Signals 20 generated by two Signal Emitters 18 is directed through a Parameter Target 22 comprised of the tissues of a patient's Finger 78. As indicated, Signal Emitters 18 include an infra-red emitting LED indicated as IR LED 80 and generating an IR Emitted Signal 82 and a red light LED indicated as Red LED 84 and generating a Red Emitted Signal 86.

IR Emitted Signal 82 and Red Emitted Signal 86 are respectively received as IR Modulated Signal 88 and Red Modulated Signal 90 by, respectively, an IR Sensor 92 and Red Sensor 94 after passing through the tissues of Finger 78. An IR Received Signal 96 and a Red Received Signal 98 are respectively generated by IR Sensor 92 and Red Sensor 94 and each of IR Received Signal 96 and Red Received Signal 98 is provided with two stages of signal amplification before being provided to Parameter Signal Processor 32 and Signal Quality Processor 38. As indicated, the first stage of signal amplification is designated as GAIN1 100 and is common to both IR Received Signal 96 and Red Received Signal 98 while the second stage of amplification, designated as IR GAIN2 102 and Red GAIN 2 104 are individual to IR Received Signal 96 and Red Received Signal 98, respectively. Including the IR LED 80 and Red LED 84 brightness controls, previously discussed with regard to Control Signal 60 output from Signal Evaluation Processor 58, the implementation illustrated in FIG. 3 provides five parameters that the system may adjust to optimize the signal quality of IR Received Signal 96 and a Red Received Signal 98, that is, the signal levels, or brightnesses, or IR LED 80 and Red LED 84, GAIN1 100, IR GAIN2 102, and Red GAIN2 104. The objective of the method and system of the present invention is to select these parameters such that IR Received Signal 96 and a Red Received Signal 98 will fall within the desired signal input range of an analog to digital (A/D) Converter 106 that generates the final signal outputs representing IR Received Signal 96 and Red Received Signal 98 to Parameter Signal Processor 32 and Signal Quality Processor 38. The selection of these parameters is of particular importance it is also an objective to place the signal levels at the highest possible level within the A/D Converter 106 input range range in order to achieve the highest resolution in the final output signals to Parameter Signal Processor 32 and Signal Quality Processor 38.

In neonates, that is, newborns, where the SpO2 sensor is placed around the foot, it is often necessary for the signal gains to be maximized and the LEDs to be tuned for the maximum emitted signal levels in order for the signals received by the Sensors 28 to have sufficient signal-to-noise ratios. However, in most other applications, the LED emitted signal levels, that is, the brightness of the LEDs, can be reduced to conserve power, which is advantageous as the LED's draw a significant amount of power from the system. As described, however, such reductions in the LED signal levels requires an intelligent system where the LED emitted signal power is controlled adaptively according to feedback derived from physiological parameters. As described, one of the signal parameters of greatest interest is the signal AC-DC modulation level (MOD) since the $SpO_2$ is an empirically derived parameter based on the ratio of modulation level (MOD) between the IR signal and the RED signal. A sufficient MOD level protects the $SpO_2$ derivation from resolution error and system noise, but increasing the LED brightness increases power demands power while reducing the LED emitted signal power levels and compensated by increasing signal amplification levels will maintain the desired MOD levels, but at the expense of possible increases in error rates or levels.

Examples of the adaptation of signal amplification and emitted signal power levels dependent upon AC-DC modulation (MOD) levels are presented in Tables A and B below, wherein Tables A and B each illustrate the operation of the present invention for two patients, designated as Subject 1 and Subject 2.

Table A illustrates the instance before activation of adaptive regulation of the emitted signal power and system amplification according to the present invention. Table B, in turn, illustrates the instance after activation, performance and completion of adaptive regulation of the emitted signal power and signal amplification according to the present invention.

In each of the examples, that is, in each of Tables A and B, the parameters of interest of Subject 1 provide a significantly high levels of AD-DC modulation (MOD). In the case of Subject 1, therefore, and because of the relatively high MOD levels of the IR Modulated Signal 88 and Red Modulated Signal 90, the emitted power levels of the IR Emitted Signal 82 and Red Emitted Signal 86 are reduced and the reduction in emitted signal level is compensated by GAIN1 100, IR GAIN2 102, and Red GAIN2 104.

In contrast, the parameters of interest for Subject 2 in each of Tables A and B result in a significantly lower level of AD-DC modulation (MOD). Because of the relatively low MOD levels of the IR Modulated Signal 88 and Red Modulated Signal 90 for Subject 2, therefore, the emitted power levels of the IR Emitted Signal 82 and Red Emitted Signal 86 are increased to enhance the signal to noise ratios of the IR Received Signal 96 and Red Received Signal 98.

TABLE A

Before Adaptive Regulation is Activated:

|  | IR MOD | RED MOD | IR LED | RED LED | GAIN1 | IR GAIN2 | RED GAIN2 |
|---|---|---|---|---|---|---|---|
| Subject 1 | 8.65 | 9.25 | 125 | 130 | 100 | 135 | 135 |
| Subject 2 | 0.35 | 0.45 | 125 | 130 | 100 | 135 | 135 |

Table A→Adaptive Regulation→Table B

TABLE B

After Completion of Adaptive Regulation:

|  | IR MOD | RED MOD | IR LED | RED LED | GAIN1 | IR GAIN2 | RED GAIN2 |
|---|---|---|---|---|---|---|---|
| Subject 1 | 8.65 | 9.25 | 95 | 100 | 118 | 150 | 149 |
| Subject 2 | 0.35 | 0.45 | 150 | 157 | 82 | 137 | 136 |

The method for determining the degree to which the emitted power levels of the IR Emitted Signal 82 and Red Emitted Signal 86 are to be reduced or increased and the degree to which the signal amplification factors GAIN1 100, IR GAIN2 102, and Red GAIN2 104 are to be adapted are based on a closed-loop feedback system of the present invention and, as described, is based on the MOD levels. It will be noted that, according to the present invention, the adaptation of emitted signal and amplification levels may perform the adaptive processes illustrated in Table A, or may continue the adaptive processes through completion of the results shown in Table B.

It will be apparent that one skilled in the arts will be able to extend the feedback parameter to include other physiological parameters in addition to the MOD, such as the current SpO2, the rate of its change, or simply the oximetric signal stability, as has been described herein above. It will also be apparent that the method and apparatus of the present invention may be implemented to include parameters from other modalities, such as EKG, non-invasive blood pressure, $EtCO_2$, or invasive arterial pressure systems and procedures. One skilled in the arts will also understand that the adaptive system of the present invention may elect or be directed to not to exercise the power conservation option if the system or an operator thereof it determines that the status of the patient is deteriorating and that power conservation measures may result in an undesired level of risk.

Since certain changes and modifications may be made in the above described invention without departing from the spirit and scope of the invention herein involved, it is intended that all of the subject matter of the above description or shown in the accompanying drawings shall be interpreted merely as examples illustrating the inventive concept herein and shall not be construed as limiting the invention.

What is claimed is:

1. A system for adjusting power employed by a light emitting device used for medical applications, comprising:
   a light emitting device;
   a power unit coupled to said light emitting device for powering the light emitting device and responsive to a control signal for adjusting power applied to the light emitting device;
   a control unit for providing the control signal and coupled to the power unit, the control signal being determined in response to an estimated signal quality value required for measuring a physiological parameter and a characteristic of a signal associated with the physiological parameter measured using light produced by the light emitting device.

2. The system according to claim 1, wherein the control signal is further determined from a monitored patient parameter.

3. The system according to claim 2, wherein the monitored patient parameter comprises at least one of:
   a blood oxygen representative parameter;
   a change in a blood oxygen representative parameter;
   a rate of change of a blood oxygen representative parameter;
   a pulse rate;
   a change in pulse rate;
   a patient temperature;
   a arterial blood pressure;
   a hematocrit level; and
   a cardiac index.

4. The system according to claim 1, wherein the characteristic of the signal associated with a measured physiological parameter comprises at least one of:
   a signal modulation characteristic;
   a signal intensity characteristic responsive to brightness of light received from said light emitting device; and
   a parameter derived from determining a quality measure indicating quality of the measured physiological parameter.

5. The system according the claim 1, wherein the control signal is further determined from monitored patient parameters.

6. The system according to claim 1, wherein:
   said control signal is determined by a comparison of a measured patient parameter with known noise characteristics of the system.

7. The system according to claim 1, wherein:
   said control signal is determined by a comparison of a measured patient parameter with measured system noise characteristics.

8. The system according to claim 1, wherein:
   the control signal is determined by a comparison of an amplitude of a modulated portion of a signal derived from patient data with one of measured system noise characteristics and known system noise characteristics.

9. In a device for monitoring a patient parameter including a signal source for emitting a monitoring signal and a sensor for receiving a modulated signal representing the emitted monitoring signal modulated by the parameter, an emitted monitoring signal controller for controlling a signal characteristic of the emitted monitoring signal, comprising:
   a parameter signal processor for receiving the modulated signal and generating a parameter output representing the parameter, a signal quality processor for measuring received signal characteristics of the modulated signal, a signal evaluation processor for evaluating the received signal characteristics of the modulated signal with respect to required signal characteristics of the modulated signal for generating the parameter output, a signal control processor for controlling an emitted signal characteristic of the emitted monitoring signal so that the received modulated signal possesses the required signal characteristics.

10. The emitted monitoring signal controller of claim 9, wherein the controlled emitted signal characteristic of the emitted monitoring signal is the emitted signal power level.

11. The emitted monitoring signal controller of claim 9, wherein the received signal characteristic of the modulated signal is at least one of:

a signal modulation characteristic;

a signal intensity characteristic responsive to brightness of light received from said light emitting device; and a parameter derived from determining a quality measure indicating quality of the measured physiological parameter.

12. The emitted monitoring signal controller of claim 10, wherein:

the emitted signal power level is decreased when the received signal characteristics of the modulated signal exceed the required signal characteristics for generation of the parameter output, and the emitted signal power level is increased when the received signal characteristics of the modulated signal are lower than the required signal characteristics for generation of the parameter output.

13. The emitted monitoring controller of claim 9, further including:

a patient environment processor for monitoring a patient condition and generating a corresponding environmental condition output representing an environmental condition of the patient affecting monitoring of the parameter, wherein the signal evaluation processor is responsive to the environmental condition output for modifying the required signal characteristics of the modulated signal accordingly.

14. The emitted monitoring signal controller of claim 13, wherein the monitored patient condition is at least one of:

a blood oxygen representative parameter;

a change in a blood oxygen representative parameter;

a rate of change of a blood oxygen representative parameter;

a pulse rate;

a change in pulse rate;

a patient temperature;

a arterial blood pressure;

a hematocrit level; and a cardiac index.

15. A method for adjusting power emitted by a light emitting device used for medical applications, comprising the steps of:

determining a characteristic of a signal associated with a physiological parameter measured using light produced by the light emitting device, generating a control signal based upon an estimated quality value for measuring a physiological parameter and the characteristic of the signal, and providing the control signal to a power unit coupled to the light emitting device and providing power to the light emitting device and adjusting the power provided to the light emitting device in accordance with the control signal.

16. The method according to claim 15, wherein the control signal is further determined from a monitored patient parameter.

17. The method according to claim 16, wherein the monitored patient parameter comprises at least one of:

a blood oxygen representative parameter;

a change in a blood oxygen representative parameter;

a rate of change of a blood oxygen representative parameter;

a pulse rate;

a change in pulse rate;

a patient temperature;

a arterial blood pressure;

a hematocrit level; and a cardiac index.

18. The method according to claim 15, wherein the characteristic of the signal associated with a measured physiological parameter comprises at least one of:

a signal modulation characteristic;

a signal intensity characteristic responsive to brightness of light received from said light emitting device; and a parameter derived from determining a quality measure indicating quality of the measured physiological parameter.

19. In a device for monitoring a patient parameter including a signal source for emitting a monitoring signal and a sensor for receiving a modulated signal representing the emitted monitoring signal modulated by the parameter, a method for controlling a signal characteristic of the emitted monitoring signal, comprising the steps of:

measuring received signal characteristics of the modulated signal, evaluating the received signal characteristics of the modulated signal with respect to required signal characteristics of the modulated signal for generating the parameter output, controlling an emitted signal characteristic of the emitted monitoring signal so that the received modulated signal possesses the required signal characteristics.

20. The method of claim 19 for controlling a signal characteristic of the emitted monitoring signal, wherein the controlled emitted signal characteristic of the emitted monitoring signal is the emitted signal power level.

21. The emitted monitoring signal controller of claim 20 for controlling a signal characteristic of the emitted monitoring signal, further comprising the steps of:

decreasing the emitted signal power level when the received signal characteristics of the modulated signal exceed the required signal characteristics for generation of the parameter output, and increasing the emitted signal power level when the received signal characteristics of the modulated signal are lower than the required signal characteristics for generation of the parameter output.

22. The method claim 19 for controlling a signal characteristic of the emitted monitoring signal, further comprising the steps of:

monitoring a patient condition and generating a corresponding environmental condition output representing an environmental condition of the patient affecting monitoring of the parameter, and modifying the required signal characteristics of the modulated signal according to the monitored patient environmental condition.

23. The method of claim 22 for controlling a signal characteristic of the emitted monitoring signal, wherein the received signal characteristic of the modulated signal is at least one of:

a signal modulation characteristic;

a signal intensity characteristic responsive to brightness of light received from said light emitting device; and a parameter derived from determining a quality measure indicating quality of the measured physiological parameter.

* * * * *